United States Patent [19]

Focella et al.

[11] 4,196,185

[45] Apr. 1, 1980

[54] IMMUNOASSAY FOR PHENCYCLIDINE

[75] Inventors: Antonino Focella, Clifton; John E. Heveran, Fairfield, both of N.J.

[73] Assignee: Hoffmann-La Roche Inc., Nutley, N.J.

[21] Appl. No.: 912,272

[22] Filed: Jun. 5, 1978

[51] Int. Cl.$^2$ ............... A61K 43/00; G01N 33/16
[52] U.S. Cl. .................. 424/1; 23/230 B; 260/112 B; 424/12; 546/194
[58] Field of Search ............... 546/191, 194; 260/112 B; 23/230 B; 424/1, 12

[56] References Cited

U.S. PATENT DOCUMENTS

| 4,000,143 | 12/1976 | Dykstra et al. | 546/194 |
| 4,038,268 | 7/1977 | Moritz et al. | 546/194 |

OTHER PUBLICATIONS

Kaur et al., J. Med. Chem., vol. 12, 1969, pp. 473–476.
Kaur et al., Theriogenology, vol. 6, Nos. 2–3, 1976, pp. 193–208.
Pearce, Clin. Chem., vol. 22, No. 10, Oct. 1976, pp. 1623–1626.

*Primary Examiner*—Benjamin R. Padgett
*Assistant Examiner*—Christine M. Nucker
*Attorney, Agent, or Firm*—Jon S. Saxe; George M. Gould; William G. Isgro

[57] ABSTRACT

An improved immunoassay for detecting the drug of abuse phencyclidine is described. This immunoassay is characterized in utilizing as reagents (i) an antibody elicited with a novel immunogen comprising 4-[(1-piperidinyl)cyclohexyl] benzoic acid covalently bonded to an immunogenic carrier material through the carboxyl group and (ii) a novel radiolabeled derivative of phencyclidine, namely $^{125}$I N-(4-hydroxy-2-phenylethyl)-4-[1-(1-piperidinyl)cyclohexyl] benzamide.

9 Claims, No Drawings

IMMUNOASSAY FOR PHENCYCLIDINE

BACKGROUND OF THE INVENTION

Phencyclidine is an anesthetic which is medicinally useful only in veterinary application. The illicit use of phencyclidine in humans produces symptoms ranging from confusion, disorientation, stupor, and coma to death in cases of overdose. The ingestion of 1 mg or "snorting" of 1–3 mg can produce physiological changes. The plasma half life of phencyclidine in humans has been reported as 11 hours. However, a confusional state may continue for as long as 15 days and a psychosis may persist for 4–5 weeks following use. Blood levels of 100 ng/ml are usually associated with coma. Due to its lipophilic nature, phencyclidine may be detected in CNS fluid and tissue when it is no longer found in blood and present only in trace amounts in urine. Phencyclidine has been identified and determined in urine at levels of less than 0.010 ng/ml to greater than 23 ng/ml. The metabolites of phencyclidine have been identified in urine as: a N-dealkylated metabolite 1-phencyclohexylamine; and two hydroxylated metabolites 1-(1-phenylcyclohexyl)-4-hydroxypiperidine and 1-(3-hydroxy-1-phenylcyclohexyl) piperidine. Phencyclidine blood, urine and tissue levels have also been compared to the clinical status and the phencyclidine concentrations were usually higher in urine than in blood.

A radioimmunoassay for phencyclidine is described by Kalir et al., Theriogenology 6, No. 2–3, 193-(1976). This assay employed an antibody elicited with an immunogen consisting of 1[1-(4-aminophenylcyclohexyl] piperidine coupled via its diazonium salt to bovine serum albumin. The labeled phencyclidine derivative employed in this assay was $^3$H-aminophencyclidine or $^3$H-phencyclidine.

DESCRIPTION OF THE INVENTION

The present invention relates to an improved immunoassay for detection of the drug phencyclidine and its metabolites. Since phencyclidine is not antigenic per se it is necessary to employ haptenic compounds derived from phencyclidine to produce immunogens which can elicit the desired phencyclidine specific antibodies for use in such immunoassay.

In a preferred embodiment of the present invention a novel hapten compound 4[-1-(piperidinyl) cyclohexyl] benzoic acid and acid addition salts thereof is useful in preparing immunogens. The aforesaid hapten is readily obtained by hydrolyzing the known 1-[1-(trifluoromethylphenyl)cyclohexyl] piperidine (Kalir et al., J. Med. Chem., 12, 473 (1969)) with strong mineral acid, e.g. concentrated $H_2SO_4$ at elevated temperature, e.g. 110° C.

In order to prepare the immunogen needed in the present invention, it is necessary that the aforesaid hapten be covalently bonded through the carboxyl group to a conventional immunogenic carrier material. As used herein, the term "immunogenic carrier material" is meant to include those materials which have the property of independently eliciting an immunogenic response in a host animal and which can be covalently coupled to the above described haptens. Suitable carrier materials include, for example, proteins; natural or synthetic polymeric compounds such as polypeptides, e.g., polylysine or copolymers of other amino acids; polysaccharides, and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin, and bovine gamma globulin. Other protein products will be suggested to one skilled in the art. It is generally preferred but not necessary that proteins by utilized which are foreign to the animal hosts in which the resulting antigen will be employed.

The covalent coupling of the hapten to the immunogenic carrier material can be carried out in a manner well known in the art for establishing amide bonds. One type of method for coupling does not require the isolation of activated intermediates. Such methods include the mixed anhydride method, the use of EEDQ (N-ethoxy-carbonyl-2-ethoxy-1, 2-dihydroquinoline) or preferably the use of EDCI (1-ethyl-3-(3-dimethylaminopropyl) carbodiimide hydrochloride as coupling agent.

Alternatively, it is possible to utilize methods involving the isolation of an activated form of the hapten prior to coupling. An example of such method involves formation and isolation of the N-hydroxy-succinimide ester.

A further aspect of the present invention resides in the use of a novel radiolabelled phencyclidine derivative in the practice of the instant immunoassay. Such novel radiolabelled phencyclidine derivative is $^{125}$I-N-(4-hydroxy-2-phenylethyl)-4-[1-(1-piperidinyl) cyclohexyl] benzamide. This material is conveniently prepared by converting the aforesaid hapten, 4-[1-(piperidinyl) cyclohexyl] benzoic acid, into its corresponding acyl halide by treatment with a suitable halogenating agent such as thionyl halide preferably through chloride. The resulting acyl halide is then reacted with tyramine under conventional Schotten-Baumann conditions to yield the desired substrate for radiolabelling.

Radioiodination of the substrate compound can be carried out by procedures well known in the art. One preferred procedure involves the use of Chloramine-T and sodium iodide-[$^{125}$I].

The immunogens of the present invention may be utilized to induce formation of antibodies specific to phencyclidine thereof in host animals by injecting the immunogen in such a host, preferably using a conventional adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with phencyclidine as described above.

The specific antibodies of the present invention are useful as reagents for the determination of phencyclidine. In such an assay, a known amount of labeled phencyclidine is mixed with the above antibody and a sample containing some phencyclidine is added. The amount of phencyclidine in the sample can be determined by measuring the inhibition of the binding to the specific antibodies of the labeled phencyclidine by the unknown sample. The reagents may be added in any order. A suitable assay procedure for this purpose is described in greater detail in U.S. Pat. No. 3,709,868.

The immunoassay of the present invention is further illustrated by reference to the accompanying Examples.

EXAMPLE 1

Preparation of 4-[(1-piperidinyl) cyclohexyl] benzoic acid sulfate

A mixture of 41.6 g of 1-[1-(trifluoromethylphenyl) cyclohexyl] piperidine and 100 ml. of concentrated $H_2SO_4$ was heated in an oil bath at 105°–110° C. for 90 minutes and cooled in an ice-bath. The reaction mixture was poured with stirring into a beaker containing 250 g of ice water and the precipitate allowed to stand for two hours, filtered and dried.

Recovery 51.6 g (99%), mp 248°–250° C.

An analylitcal sample recrystallized from ethanol melted at 242°–243° C.

EXAMPLE 2

Preparation of N-(4-hydroxy-2-phenylethyl)-4-[1-piperidinyl) cyclohexyl] benzamide A mixture of 3 g (7.78 mm) of 4-[(1-piperidinyl) cyclohexyl] benzoic acid sulfate, 150 ml of toluene, and 5 ml of thionyl cloride was refluxed for 5 hours and the volatiles removed under reduced pressure. The acyl chloride residue was dissolved in 10 ml of $CHCl_3$ and added dropwise simultaneously with 10 ml of a 10% NaOH solution to a well stirred solution of 1.6 g (11.7 mm) of tyramine in 200 ml of $CHCl_3$ and 100 ml of $H_2O$ cooled on an ice-bath. After the addition was complete (about 1 hr) the reaction mixture was allowed to stir at room temperature for 4 hours and the pH adjusted to about 7 by the dropwise addition of acetic acid. The small particles to tarry material formed were removed by filtration and the organic phase separated, washed with 2×75 ml of $H_2O$ and dried over $Na_2SO_4$. The volatiles were removed under reduced pressure and the amorphous solids (3 g) were crystallized twice with $CH_3CN$ to provide 2.1 g (66.1%) of N-(4-hydroxy-2-phenylethyl)-4-[1-(1-piperidinyl)cyclohexyl] benzamide melting at 123°–125° C.

EXAMPLE 3

PREPARATION OF IMMUNOGEN (PHENCYCLIDINE-BSA CONJUGATE)

A total of 250 mg of 4-[(1-piperidinyl)] benzoic acid sulfate ¼ M hydrate was dissolved in 25 ml dimethylsulfoxide and diluted in 100 ml with 0.85% NaCl. The pH was adjusted to 4 using 2.5% NaOH and 500 mg of bovine serum albumin (BSA-Pentex Fraction V or equivalent) was slowly added to the solution while constantly monitoring pH at approximately 4 using dilute HCl. A total of 200 mg of 1-ethyl-3-(3-dimethylaminopropyl) carbodiimide HCl (EDCI) was slowly added to the solution while maintaining pH at approximately 4 as above. The mixture was adjusted to pH 4.5 with 2.5% NaOH and continuously stirred for 24 hours at room temperature. The solution was transferred to a dialysis bag (Spectrum Medical Industries Spectrapor #2) and dialyzed against distilled water (6×) for 2 days and then against 85% NaCl (4×) for 2 days at room temperature. The dialyzate was tested by immunoelectrophoresis (0.05 ionic strength, pH 8.6 buffer, 1% aqueous gel plates and goat anti-BSA serum) and a precipitin band indicated that the immunogen was distinctly different from BSA.

EXAMPLE 4

PREPARATION OF ANTISERUM

Rabbits were injected at one week intervals for three weeks with 1 ml of phencyclidine-BSA conjugate prepared as an emulsion (1:1) in Freund's complete adjuvant, into four sites (axillary and inguinal lymph regions). Additional 1 ml subcutaneous immunizations at each of four sites were carried out at weekly intervals for at least two months. Subsequent injections were made at monthly intervals with immunogen in incomplete adjuvant. Bleedings were obtained by venipuncture and serum was collected in 50 ml vacuum serum bottles at monthly intervals.

Bleedings, obtained from immunized rabbits were allowed to stand at 2°–8° C. temperature until the clot had formed. The serum was decanted into 50 ml conical flasks and stored at from −20° to 5° C.

EXAMPLE 5

Preparation of $^{125}$I-N-(4-hydroxy-2-phenethyl)-4-[(1-piperidinyl) cyclohexyl] benzene acid sulfate A total of 50 μl of a solution of 1 mg of -N-(4-hydroxy-2-phenethyl) 4-[(1-piperidinyl) cyclohexyl] benzoic acid sulfate in 1 ml of 10% ethyl acetate-90% water was added to a vial containing 5 mCi $Na^{125}I$ having a radioactive concentration of >100 mCi/ml. To this mixture was then added a total of 40 μl of chloramine T solution (0.5%). The reaction mixture was mixed for 90 seconds. After mixing a total of 40 μl of a 1% solution of sodium meta bisulfite was added to the reaction vial and the vial contents were mixed for 30 seconds to step the reaction.

The mixture was removed from the vial and placed on the surface at a Bio-Gel P-2 column (2.6×40 cm, 100–200 mesh) until completely absorved on the column bed. Approximately 2 ml of Tris buffer (0.1 M, ph 7.0) was added to the column. The column was then eluted with Tris buffer and 80×5 ml fractions were collected. The eluate contained the above captioned labeled antigen, fractions of which bound >50% of the rabbit antiserum.

EXAMPLE 6

IMMUNOASSAY PROCEDURE

BASIC PRINCIPLE

The radioimmunoassay for phencyclidine and its metabolites is based on the competitive binding to antibody of ratiolabeled antigen an unlabeled antigen in proportion to their concentration in the solution.

The methodology of the RIA system utilizes four reagents:

(1) substance to be measured, called unlabeled antigen (the phencyclidine or phencyclidine metabolite in the subject's specimen);

(2) The labeled antigen (phencyclidine derivative N-(4-hydroxy-2-phenylethyl) 4-[1-piperidinyl)cyclohexyl] benzamide which has been labeled with the radioactive isotope, $^{125}$I);

(3) Antiserum that is specific for the antigen (phencyclidine);

(4) A reagent to separate antigen (both labeled and unlabeled) bound to the antibody from the unbound antigen.

For the test, an unknown specimen is added to a test tube containing known amounts of phencyclidine antibodies and radio-labeled antigen. After an incubation period (to allow the unlabeled antigen and labeled antigen to compete for the phencyclidine antibodies) the bound antigen is then separated from the free antigen by precipitation of the antibody complexes with saturated ammonium sulfate. After centrifugation, the supernatant fluid, which contains the free antigen, is transferred to test tubes and measured in a gamma scintillation counter. A A positive specimen is identified qualitatively where the radioactivity is equal ot or greater than that of the positive control and quantitatively by comparison to a standard curve. For optimal results, the prescribed protocol must be followed carefully.

Test Procedure:
Materials Utilized:
1 vial containing 20 ml phencyclidine antiserum (rabbit) diluted 1/1000 in 0.5 M phosphate saline buffer with 0.1% sodium azide. 1 vial containing 20 ml $^{125}I$ phencyclidine derivative at a concentration of 410,000 DPM/ml in 0.5 M phosphate saline buffer with 0.1% sodium azide. 1 vial containing 4 ml positive phencyclidine urine control with 0.1% sodium azide.

1 vial containing 4 ml normal human urine control phencyclidine with 0.1% sodium azide.

1 vial containing 50 ml saturated ammonium sulfate solution.

The above basic kit contains all reagents necessary for the assay, supplied in excess to assure sufficient material for at least 100 test tubes.

Equipment Required:
Test tubes: 10×75 or 12×75 disposable.
Pipettes:
  Semiautomatic pipettes (e.g. Schwarz/Mann Biopette, Eppendorf pipettes, etc.) or automatic diluting equipment, or glass transfer pipettes (e.g., Lang-Levy or Kirk pipettes).
  Do *not* use serological blowout type pipettes.
Mixer:
  Vortex-type mixer.
Centrifuge:
  Almost any type which
    generates 1200 to 2500×g using a swinging bucket rotor
    generates 3500 to 4000×g using a fixed angle head rotor.
The swinging bucket rotor is preferred because the pellet is formed at the bottom of the test tube and the supernatant is more easily removed than when the pellet is formed at an angle. If a centrifuge with less gravitational force is used, centrifugation time must be extended until suitable pellets are formed.
Counter:
Gamma scintillation counter.
Temperature requirements:
Ambient temperature is recommended throughout the procedure, temperature control is not critical at any step.
Assay:

1. Set up and label as many tubes as are required for the phencyclidine positive control and for assays of unknown urine specimens. Because of the importance of control values in the determination, it is recommended that the positive control be done in triplicate.

2. Add 0.1 ml of positive phencyclidine urine control to each of three tubes.

3. Add 0.1 ml of each unknown urine specimen to remaining numbered tubes.

4. Add 0.2 ml of the $^{125}I$ phencyclidine derivative to each tube; mix well on vortex-type mixer.

5. Add 0.2 ml of the phencyclidine antiserum to each tube, mix well on vortex-type mixer.

6. Incubate tubes at ambient temperature for 10 minutes.

Timing: Incubation time should be no less than 10 minutes but can be extended to any time interval up to 24 hours. Time element is not critical. When incubation time is less than one hour, as in the case of testing for a suspected overdose of phencyclidine samples and standards must be incubated for exactly the same period of time.

7. Add 0.5 ml of supernatant fluid from saturated ammonium sulfate sodium to each tube to precipitate globulins; mix well on vortex-type mixer.

8. Allow tubes to stand at ambient temperature for a minimum of 10 minutes to complete precipitation.

Once saturated ammonium sulfate solution has been added to stop reaction, at least 10 minutes should be allowed for precipitation. (In cases where speed is critical, a 5-minute incubation period can be employed but is not generally recommended.)

9. Centrifuge for 10 minutes, at approximately 1200 to 2500×g with a swinging bucket rotor, or at 3500 to 4000×g with a fixed angle head rotor. (Swinging bucket rotor is preferable.)

10. Withdraw 0.5 ml of supernatant fluid from each tube without disturbing precipitate along sides or at bottom (supernatant fluid must be clear). Withdraw supernatant as soon as possible after centrifugation. If left for extended periods, pellet may soften and start to flake. Transfer to appropriate tube for counting.

11. Count each tube in gamma scintillation counter for one minute to obtain counts per minute (CPM).

Evaluation:
Compare counts per minute obtained from each unknown specimen with average CPM contained from phencyclidine positive controls.

Negative Results:
The test is negative for the presence of phencyclidine when the unknown specimen CPM is lower than that of the average CPM of the phencyclidine positive control.

Positive Results:
The test is positive when the unknown specimen CPM is equal to or higher than that of the average CPM of the phencyclidine positive control.

Quantitative Test:
The radioimmunoassay (RIA) for phencyclidine protocol presented here describes a qualitative test. If there is need of quantitation, the following modification of the above procedure may be used to establish a standard curve in place of only positive controls.

To establish a standard curve: The normal urine control (supplied in kit) is used as the 0 point on the standard curve and as the diluent for preparing other standard solution. The phencyclidine positive control urine contains 100 ng of phencyclidine/ml and is to be used as that standard. A 1:2 dilution of the 100 ng/ml standard in the normal urine control will provide a 50 ng/ml standard solution. A 1:4 dilution of the 100 ng/ml standard in the normal urine control will provide a 25 ng/ml standard solution. A 1:8 dilution of the standard in the normal urine control will provide a 12.5 ng/ml standard solution. Results obtained for a representative run are summarized below in the table:

| Phencyclidine Concentration vs Response | |
|---|---|
| Concentration (ng/ml) | DPM |
| 0 | 5131 |
| 12.5 | 12375 |
| 25 | 15168 |
| 50 | 17617 |
| 100 | 22412 |
| 200 | 25216 |

Set up and label 15 (10×75 mm) test tubes. To tubes #1, 2 and 3, add 0.1 ml each of normal urine control to tubes #4, 5 and 6, add 0.1 ml each of the 12.5 ng/ml phencyclidine standard to tubes #7, 8 and 9, add 0.1 ml each of the 25 ng/ml barbiturate standard to tubes #10, 11 and 12, add 0.1 ml each of the 50 ng/ml phencyclidine standard, and to tubes #13, 14 and 15, add 0.1 ml each of the 100 ng/ml standard.

Proceed with steps 4 to 11 in the above protocol.

Set up standard curve as follows: Let the Y (vertical) axis indicate CPM and X (horizontal) axis indicate ng phencyclidine/ml. Plot points showing the average CPM of three tubes containing normal human urine, the average of the three containing 12.5 ng/ml standards, the average of the three containing 25 ng/ml the average of the three containing 50 ng/ml standards and the average of the three containing 100 ng/ml standards. Fit the best line to establish a curve.

To determine the phencyclidine concentration: Determine CPM for each urine specimen tested. Read across from Y axis to determine ng/ml of equivalents present in tested urine.

If the sample urine value is higher than 500 ng/ml, dilute the test specimen 1:5 and 1:10 in the normal urine control and repeat the test. If the value now falls within the standard curve, multiply the ng/ml by the appropriate dilution factor to establish the phencyclidine concentration in the undiluted urine. Higher dilution may be necessary.

Test Modifications:

The following modifications may be instituted in order to shorten the time required for performing the assay. This is especially important for those who must process large number of samples.

Counting Time:

It has been determined that the counting time required to achieve statistically accurate results may be reduced to 0.1 minute per sample. It is recommended that when borderline samples are encountered, the controls and the borderline samples be recounted for one minute for maximum statistical accuracy.

For Higher Cutoff Levels:

Should it be considered desirable to establish a cutoff level higher than 100 ng/ml, this can be done by diluting the urine sample with normal urine and using 0.1 ml of the diluted sample in Step 3 of the Test Procedure (e.g. a dilution of 1:5 will provide a cutoff level of 500 ng/ml).

Alternatively, a smaller volume of the sample urine, instead of dilution, may be used in achieving a higher cutoff level (e.g. a 0.02 ml urine sample would result in a cutoff level of 500 ng/ml). However, the use of small sample volumes is more likely to result in significant pipetting errors.

Test Limitations:

Based on the values obtained with pre-drug urines from individuals receiving phencyclidine and subjects taking specific drugs, as well as the distribution of the phencyclidine values observed with urines from a normal population, a cutoff between a positive and a negative urine has been set at 100 ng phencyclidine equivalents/ml.

Expected Values:

The radioimmunoassay for phencyclidine has been evaluated using urines from a random population of normal individuals, using urines from individuals receiving known amounts od drugs other than phencyclidine using urines from individuals known to contain phencyclidine.

Study One+:

Employing a level of 100 ng/ml of urine as the cutoff level, over 457 "normal" urines from a random population were tested for phencyclidine equivalents. All urines were negative. The highest values obtained were equivalent to 25 ng phencyclidine/ml, respectively, most other urines contained less than 5 ng phencyclidine equivalents/ml. (See Table 1 for a summary of results.)

A number of metabolites are found in urine following oral administration of phencyclidine. Since the number and proportion of these metabolites vary with each subject, the results are expressed in terms of equivalents of the unlabeled standard, phencyclidine, per ml (PCP E/ml).

Study Two+:

Using a level of 100 phencyclidine equivalents/ml as the cutoff point, no cross-reactivity was observed in patents taking standard doses of:

| | |
|---|---|
| aminopyrine | methaquolone |
| amphetamine | methyprylon |
| caffeine | methadone |
| chlordiazepoxide HCl | morphine |
| chloroquine | oxyphenbutazone |
| chlorprormazine | phenobarbital |
| diazepam | phenylbutazone |
| diphenylhydantoin | promethazine |
| flurazepam HCl | quinine sulfate |
| glutethimide | secobarbital |
| imipramine HCl | thioridazine HCl |
| | trifluoperazine HCl |

Table I

| Normal Urine Specimens | |
|---|---|
| PCP (ng/ml) | Percentage |
| 0 | 89.5% |
| 0–5 | 6.1% |
| 5–10 | 2.4% |
| 10–15 | 1.5% |
| 15–20 | 0.2% |
| 20–25 | 0.2% |

We claim:

1. N-(4-hydroxy-2-phenylethyl)-4-[1-(1-piperidinyl)-cyclohexyl] benzamide.

2. $^{125}$I-N-(4-hydroxy-2-phenylethyl)-4-[1-(1-piperidinyl) cyclohexyl] benzamide.

3. An immunogen consisting of 4-[1-(piperidinyl) cyclohexyl] benzoic acid covalently liked through its carboxyl group to an immunogenic carrier material.

4. The immunogen of claim 3 wherein said immunogenic carrier material is bovine serum albumin.

5. A method for the assay of phencyclidine in a sample which method comprises mixing said sample with known amounts of a $^{125}$I-labelled phencyclidine derivative and an antibody which will selectively complex with phencyclidine, said antibody being elicited in the blood of a host animal by immunization with the immunogen of claim 3, separating antibody bound antigen from free antigen and then measuring the radioactivity of either the free or bound antigen and comparing said value to values obtained previously with samples containing known amounts of phencyclidine.

6. The method of claim 5 wherein said $^{125}$I-labelled derivative is $^{125}$I-N-(4-hydroxy-2-phenylethyl)-4-[1-(-piperidinyl) cyclohexyl] benzamide.

7. The method of claim 6 wherein the antibody bound antigen is separated from free antigen by precipitation by ammonium sulfate, the precipitate is centrifuged and the supernatant counted.

8. The method of claim 7 wherein phencyclidine is assayed qualitatively by comparing the counts obtained to a positive control, whereby counts equal or greater to said control value indicates the presence of phencyclidine in the sample.

9. The method of claim 7 wherein phencyclidine is assayed quantitatively by comparing the counts obtained to a standard curve.

* * * * *